US012753144B2

(12) United States Patent
Khramov et al.

(10) Patent No.: US 12,753,144 B2
(45) Date of Patent: Oct. 6, 2026

(54) PROCESS FOR PRODUCING HEXAMETHYLENEDIAMINE FROM CAPROLACTAM

(71) Applicant: Ascend Performance Materials Operations LLC, Houston, TX (US)

(72) Inventors: Mikhail I. Khramov, Houston, TX (US); Scott G. Moffatt, Houston, TX (US); C. Alex Diaz, Houston, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 380 days.

(21) Appl. No.: 18/486,463

(22) Filed: Oct. 13, 2023

(65) Prior Publication Data

US 2024/0124386 A1 Apr. 18, 2024

Related U.S. Application Data

(60) Provisional application No. 63/416,121, filed on Oct. 14, 2022.

(51) Int. Cl.
*C07C 209/68* (2006.01)
*C07C 253/00* (2006.01)
*C07C 253/34* (2006.01)

(52) U.S. Cl.
CPC .......... *C07C 209/68* (2013.01); *C07C 253/00* (2013.01); *C07C 253/34* (2013.01)

(58) Field of Classification Search
CPC .... C07C 209/68; C07C 253/00; C07C 253/34
See application file for complete search history.

(56) References Cited

U.S. PATENT DOCUMENTS

| | | | | | |
|---|---|---|---|---|---|
| 2,234,566 | A | * | 3/1941 | Lasier | C07C 209/48 558/310 |
| 2,900,310 | A | * | 8/1959 | Ottenheym | C07C 255/00 558/310 |
| 3,855,267 | A | * | 12/1974 | Cobb | B01J 27/18 558/310 |
| 5,455,346 | A | * | 10/1995 | Kopietz | C08J 11/16 562/487 |

FOREIGN PATENT DOCUMENTS

| | | | | | |
|---|---|---|---|---|---|
| CN | 111574401 | A | * | 8/2020 | C07C 231/02 |
| JP | 2008255554 | A | * | 10/2008 | |
| WO | 96/18614 | | | 6/1996 | |
| WO | WO-2014179070 | A1 | * | 11/2014 | C08J 3/12 |

OTHER PUBLICATIONS

CN111574401A_EnglishTranslation_Google Translate (Year: 2020).*
JP2008-255554A_EnglishTranslation_Google Translate (Year: 2008).*
CN111574401A—English Translation (Year: 2020).*
JP2008255554A_English Translation (Year: 2008).*
International Search Report for international application No. PCT/US2023/076802 mailed on Feb. 5, 2024.

* cited by examiner

*Primary Examiner* — Jeffrey S Lundgren
*Assistant Examiner* — W. Justin Youngblood
(74) *Attorney, Agent, or Firm* — Womble Bond Dickinson (US) LLP

(57) ABSTRACT

A process for converting caprolactam to aminocapronitrile, the process comprising contacting a caprolactam feed with ammonia and an aluminosilicate zeolite catalyst to produce an aminocapronitrile product, wherein the catalyst comprises less than 5 wt. % of an active metal, and wherein conversion is greater than 50% and selectivity for aminocapronitrile is greater than 91%.

20 Claims, No Drawings

PROCESS FOR PRODUCING HEXAMETHYLENEDIAMINE FROM CAPROLACTAM

CROSS-REFERENCE TO RELATED APPLICATION

This application claims priority from U.S. Provisional Application No. 63/416,121 entitled "Process For Producing Hexamethylenediamine From Caprolactam" filed Oct. 14, 2022, the disclosure of which in incorporated herein by reference in its entirety.

FIELD

The present disclosure provides a process for producing hexamethylene diamine from caprolactam via an intermediate, such as aminocapronitrile (ACN). Specifically, the present disclosure provides a gas phase process for converting caprolactam to ACN in the presence of an unmodified aluminosilicate zeolite catalyst. The ACN may then be converted to hexamethylenediamine (HMD).

BACKGROUND

The conversion of caprolactam to ACN (and subsequently to hexamethylenediamine (HMD)) is a known reaction. HMD may be used to provide starting materials for many industrial reactions including the production of polyamide-6,6 and other polymers, the production of hexamethylene diisocyanate, which is in turn used in the manufacture of polyurethanes. Some conventional processes may conduct the reaction over modified or doped catalysts. Such catalysts often comprise a base catalyst with heavy loadings of expensive, active metals. The use of these modifiers may contribute to added expense or need for further purification of the resultant product.

CN107602416A discloses a vapor phase method to prepare 6-aminocapronitrile from caprolactam as raw material that comprises S1: caprolactam vapor is mixed with hot ammonia by certain mass ratio; S2: the mixture of the caprolactam obtained in step S1 and hot ammonia are subjected to ammonification dehydration under the conditions of existing for catalyst to obtain an ammonification effluent; and S3: separating/purifying of the ammonification effluent obtained in step S2 to yield pure 6-aminocapronitrile. The method purports to be simple and to provide for high conversion ratio, e.g., up to more than 96%.

U.S. Pat. No. 3,886,196 discloses the catalytic ammonialytic cleavage of lactams to yield aminonitriles. The catalysts used in the process are magnesium-aluminum-phosphate silicates on alumina, silica, or a substrate containing alumina or silica.

Even in view of the known processes, the need exists for processes for converting caprolactam to ACN (and optionally further converting to HMD), e.g., via ammonialytic cleavage of lactams, without requiring expensive modifications to the base catalyst, e.g., added active metals and/or phosphorous.

SUMMARY

The disclosure relates to a gas-phase process for converting caprolactam to 6-aminocapronitrile (6-ACN) that comprises the step of contacting, optionally conducted at a temperature ranging from 300° C. to 450° C., caprolactam with ammonia and a catalyst, e.g., an aluminosilicate zeolite catalyst, to produce a 6-ACN product. The catalyst comprises less than 5 wt. % of an active metal and/or less than 1 wt. % phosphorous. The aluminosilicate zeolite catalyst may have a silica to alumina ratio (SAR) less than 200. In some cases, the disclosure relates to a gas-phase process for converting caprolactam to a 6-ACN product, the process comprising the steps of contacting a caprolactam feed comprising less than 100 wt % caprolactam, optionally comprising recycled PA6, or 6-aminocaproic acid, or a mixture thereof, and greater than 100 ppm impurities, comprising 6-aminocaproic acid, caprolactam dimers, N-methylcaprolactam, N-ethylcaprolactam, or combinations thereof, with ammonia and a catalyst to produce a 6-ACN product. The impurities may comprise less than 10 wt. % of low boiling impurities having a boiling point less than 255° C., measured at atmospheric pressure and/or less than 10 wt % intermediate boiling point impurities having a boiling point ranging from 255° C. to 270° C. and/or less than 20 wt. % of high boiling point impurities having a boiling point greater than 270° C., measured at atmospheric pressure. The processes may further comprise the step of purifying the 6-ACN product, preferably via distillation.

In some cases, the disclosure relates to an integrated process for converting polyamide-6 (PA6) to hexamethylenediamine, the process comprising the steps of depolymerizing a stream comprising PA6 and impurities to produce a depolymerized stream comprising caprolactam monomers, dimers, oligomers, or combinations thereof; contacting the depolymerized stream with ammonia and an aluminosilicate zeolite catalyst comprising less than 5 wt. % of an active metal to produce a 6-ACN product; (and optionally purifying the 6-ACN product, preferably by distillation and/or hydrogenating the 6-ACN product in the presence of a nickel-based catalyst to provide hexamethylenediamine); optionally reacting the 6-ACN product to produce hexamethylenediamine; and reacting the 6-ACN product and/or the hexamethylenediamine to form a subsequent reaction product. In some cases, the reacting of the 6-ACN product and/or the hexamethylenediamine may comprise reacting the hexamethylenediamine to form non-PA6 polyamides, e.g., PA6,6; PA6,10; PA6,12; and co- and terpolymers thereof, hexamethylene diisocyanate, or polyurethanes.

DETAILED DESCRIPTION

Introduction

As noted above, conventional processes for converting caprolactam to ACN (and subsequently to HMD) exist. These processes require expensive catalyst compositions that comprise a base catalyst and heavy loadings of expensive modifiers, e.g., active metals or other synergists such as phosphorus.

One example of a conventional catalyst composition comprises a base catalyst, e.g., silica or alumina that is modified with high content of an active metal such as an alkaline earth oxide. Suitable oxides include magnesium oxide, calcium oxide, strontium oxide, and barium oxide as well as transition metal oxides such as iron oxide, manganese oxide, zirconium oxide, cerium oxide, copper oxide, titanium oxide, zinc oxide, and combinations of all of these. Another conventional catalyst composition comprises an alumina or silica base catalyst that is loaded with high content of magnesium and/or phosphorus.

The use of these modifiers complicates production, contributes to added expense, and/or necessitates further purification of the resultant product. While these catalysts provide some degree of catalysis of the caprolactam-to-ACN reaction, there is room for improvement, e.g., improvements in selectivity, conversion, and catalyst life/longevity.

The inventors have now found that processes that employ the catalysts disclosed herein provide for significant improvements in catalysis of the reaction of caprolactam to ACN (and subsequently to HMD). In some cases, a process that employs catalyst, e.g., an aluminosilicate zeolite catalyst, with little if any (dopant) modification, under the conditions disclosed herein contributes to notable improvements in caprolactam conversion and/or selectivity to 6-ACN, as well as a surprising extension of catalyst life. In fact, the use of the disclosed unmodified catalysts has been found to unexpectedly improve reaction performance, even in the presence of lower purity starting material.

Without being bound by theory, it is posited that the disclosed catalysts perform well because the exposed Lewis acid centers may promote both dehydration and ammoniation reactions. It is further postulated that loading or modifying the base catalyst may adversely affect the Lewis acid centers, thereby leading to a deleterious reduction in their reactive potential.

Conventional feed streams are often high purity caprolactam feed streams. In contrast, the processes disclosed herein may advantageously use lower purity caprolactam feed streams. Without being bound by theory, it is postulated that impurities in the feed stream may poison active metal sites on conventional catalysts. The catalysts of the present disclosure, which comprise low amounts of active metals, may be less prone to catalyst poisoning and more tolerant of impurities in the feed stream while maintaining performance. Conventionally-used high purity streams detrimentally require significant purification to arrive at the high purity level. And these purification steps add complication and cost to the overall process. The surprising reaction efficiency e.g., conversion and selectivity, when utilizing the disclosed catalysts (even when using lower purity feed streams) provides for increased efficiency, process simplification, and decreased overall cost of operation.

The disclosure relates to a process, in some cases conducted in the gas phase, for converting caprolactam to an ACN product, e.g., a 6-ACN product. The process comprises the step of contacting caprolactam with ammonia over a catalyst (thus effectuating the reaction) to produce the ACN product, e.g., the 6-ACN product. The ACN product thus formed may then be converted to HMD, e.g., via hydrogenation. The catalyst is described in detail below. In some embodiments, the catalyst advantageously comprises little, if any, of an active metal, e.g., less than 5 wt. % of an active metal, and/or little, if any, of other synergists, e.g., phosphorus. The use of the disclosed catalyst has been unexpectedly found to contribute to the aforementioned improvements in reaction efficiency and catalyst life.

Catalyst

As noted above, the catalyst comprises a base catalyst and little, if any, active metal. In some cases, the base catalyst may comprise a zeolite catalyst. Many zeolite catalysts are known. For example, the base catalyst may comprise MFI (ZSM-5), FAU (faujasite, USY), *BEA (beta), MOR (high-silica mordenite), or FER (high-silica ferrierite), or combinations thereof. In an embodiment, the base catalyst comprises (or consists of) is a ZSM catalyst.

It has been discovered that the disclosed (base) catalysts are particularly effective in the aforementioned reaction. Conventional process employ catalysts that comprise higher amounts of synergists or active metals. As noted above, the performance benefit is surprising because the lack of modifiers would be expected to hinder performance.

Examples of active metals that are conventionally used (but which are minimized in the disclosed catalyst) include alkaline earth metals, transition metals, or rare earth metals, or combinations thereof. In some cases, the active metals include magnesium, calcium, iron, manganese, titanium, zirconium, or cerium, or combinations thereof.

In other unrelated, conventional reactions, e.g., hydrocarbon cracking, aluminosilicate zeolite catalysts with little, if any, metal loading are known to be employed. However, these reactions are unrelated to the caprolactam-to-ACN reaction, and as such, are not relevant to this disclosure.

The amount of active metals in the catalyst can range from 0 to 5 wt. %, e.g., from 1 ppb to 4 wt. %, from 10 ppb to 2 wt. %, from 100 ppb to 1 wt. %, from 1 ppm to 5000 ppm, from 10 ppm to 2500 ppm, from 50 ppm to 1000 ppm, from 100 ppm to 500 ppm, or from 150 ppm to 250 ppm. In terms of upper limits, the amount of active metals in the catalyst can be less than 5 wt. %, e.g., less than 4 wt. %, less than 2 wt. %, less than 1 wt. %, less than 5000 ppm, less than 2500 ppm, less than 1000 ppm, less than 500 ppm, less than 250 ppm, less than 100 ppm, less than 50 ppm, or less than 10 ppm. In terms of lower limits, the amount of active metals in the catalyst can be greater than 1 ppb, e.g., greater than 10 ppb, greater than 100 ppb, greater than 1 ppm, greater than 10 ppm, greater than 50 ppm, greater than 100 ppm, greater than 250 ppm, greater than 500 ppm, greater than 1000 ppm, or greater than 2500 ppm. Lower amounts, e.g., less than 1 ppb, and higher amounts, e.g., greater than 5 wt. %, are also contemplated.

In addition to comprising little, if any, active metals, the disclosed catalyst may comprise little, if any, synergists. One example of a synergist is phosphorus. The amount of phosphorous present in the catalyst can, for example, range from 0 to 1 wt. %, e.g., from 1 ppb to 5000 ppm, from 10 ppb to 2500 ppm, from 100 ppb to 1000 ppm, from 1 ppm to 500 ppm, from 50 ppm to 250 ppm, or from 100 ppm to 200 ppm. In terms of upper limits, the amount of phosphorous present in the catalyst can be less than 1 wt. %, e.g., less than 5000 ppm, less than 2500 ppm, less than 1000 ppm, or less than 500 ppm, less than 250 ppm, less than 100 ppm, less than 50 ppm, or less than 10 ppm. In terms of lower limits, the amount of phosphorous present in the catalyst can be greater than 1 ppb, e.g., greater than 10 ppb, greater than 100 ppb, greater than 1 ppm, greater than 10 ppm, greater than 25 ppm, greater, than 50 ppm, greater than 100 ppm, or greater than 250 ppm. Lower amounts, e.g., less than 1 ppb, and higher amounts, e.g., greater than 1 wt. %, are also contemplated. In an embodiment, the amount of phosphorous present in the catalyst is less than 1 ppm.

The silica to alumina ratio (SAR) of the catalyst can, for example, range from 25 to 200, e.g., from 40 to 150, from 50 to 125, or from 75 to 100. In terms of upper limits, the SAR of the catalyst can be 200 or less, e.g., 150 or less, 125 or less, or 100 or less. In terms of lower limits, the SAR of the catalyst can be greater than 25, e.g., greater than 40, greater than 50, or greater than 75. Lower ratios, e.g., less than 25, and higher ratios, e.g., greater than 200, are also contemplated.

Lower Purity Caprolactam Feed

In some embodiments, the caprolactam starting materials need not be of high purity, as is conventional. This has been found to be beneficial because the formation of high purity streams often requires significant processing, which may be costly and complicated. When the disclosed process is employed, lower purity caprolactam feed may be used and similar, if not improved, reaction parameters are demonstrated.

In some cases, the contacting step employs a low purity caprolactam feed comprising less than 100 wt % caprolactam and greater than 100 ppm impurities, with ammonia over the disclosed catalyst (thus effectuating the reaction) to produce the ACN product, e.g., the 6-ACN product. In some embodiments, the caprolactam feed may have a purity less than 99.99%, e.g., less than 99.9%, less than 99.5%, less than 90%, less than 85%, less than 80%, less than 75%, less than 70%, less than 65%, or less than 60%. In terms of upper limits, the caprolactam feed may have a purity of less than 99.99%, e.g., less than 99.9%, less than 99.5%, less than 99%, or less than 90%. In terms of lower limits, the caprolactam feed may have a purity of greater than 60%, e.g., greater than 65%, greater than 70%, greater than 75%, greater than 80%, or greater than 85%.

The amount of impurities in the caprolactam feed stream can, for example, range from 100 ppm to 40 wt. %, e.g., 250 ppm to 35 wt. %, 500 ppm to 30 wt. %, 1000 ppm to 25 wt. %, 2500 ppm to 20 wt. %, 5000 ppm to 15 wt. %, 1 wt. % to 10 wt. %, 100 ppm to 5 wt %, 500 ppm to 4 wt %, 0.1 wt % to 4 wt %, 0.1 wt % to 3 wt %, or 0.5 wt % to 3 wt %. In terms of upper limits, the amount of impurities in the caprolactam feed stream can be less than 40 wt. %, e.g., less than 35 wt. %, less than 30 wt. %, less than 25 wt. %, less than 20 wt. %, less than 15 wt. %, less than 10 wt %, less than 5 wt %, less than 3 wt %, less than 2 wt %, or less than 1 wt %. In terms of lower limits, the amount of impurities in the caprolactam feed stream can be greater than greater than 100 ppm, e.g., greater than 250 ppm, greater than 500 ppm, greater than 1000 ppm, greater than 2500 ppm, greater than 5000 ppm, or greater than 1 wt. %. Lower amounts, e.g., less than 100 ppm, and higher amounts, e.g., greater than 40 wt. %, are also contemplated. The ranges and limits mentioned herein are applicable to individual impurities and to impurities as a whole.

In some cases, the impurities comprise 6-aminocaproic acid, caprolactam dimers, N-methylcaprolactam, or N-ethylcaprolactam, or combinations thereof. Other impurities are contemplated, and examples of which are provided herein.

The impurities in the caprolactam feed stream may be derived from depolymerization of PA6, and may comprise 6-aminocaproic acid, caprolactam dimers, caprolactam oligomers, N-methylcaprolactam, N-ethylcaprolactam, hexenoic acid, cyclohexylamine, hexamethylenediamine, or acetic acid, or combinations thereof, for example. In some cases, the feed stream may comprise impurities derived from components other than PA 6, such as 1,3-diphenylpropane, styrene dimers, styrene-butadiene oligomers, aliphatic alcohols such as 1-decanol and 1-dodecanol, or carboxylic acids or combinations thereof, for example. In some embodiments, the caprolactam feed stream may comprise depolymerized PA6 as the impurity. In an embodiment, the caprolactam feed stream comprises caprolactam monomers, caprolactam dimers, and caprolactam oligomers.

Further impurities may include 6-methylvalerolactam, N-pentylacetamide, N-phenylacetamide, N-methylcaproamide, cyclohexanone, cyclohexenone, n-hexanenitrile, 5-hexenenitrile, or 1,2,3,4,6,7,8,9-octahydrophenazine, or combinations thereof. The impurities, in some cases, may include amines, such as 3-N-methyl-4,5,6,7-tetrahydrobenzimidazole; caprolactams such as 1,3,4,5-tetrahydroazepine-2-one, 1,5,6,7-tetrahydroazepine-2-one and structural isomers thereof; or methylcaprolactams such as 7-methylcaprolactam and 3-methylcaprolactam, or combinations thereof.

As noted above, the catalysts of the present disclosure, advantageously, may be less prone to catalyst poisoning and more tolerant of such impurities.

In an embodiment, the caprolactam feed stream comprises caprolactam, 6-aminocaproic acid, hexenoic acid, caprolactam dimers, N-methylcaprolactam, or N-ethylcaprolactam, or combinations thereof.

In some cases, the caprolactam starting materials may be derived from recycled caprolactam. Recycled caprolactam may be obtained from a variety of sources including, for example, fishing nets; fibers, e.g., clothing, carpet or filters; films; coatings; and reaction waste products; and from the processes for producing these.

The impurities may be characterized as low boiling point impurities, intermediate boiling point impurities, and/or high boiling point impurities. Low boiling point impurities are those with a boiling point less than that of ACN, e.g., less than 255° C. at atmospheric pressure. In terms of ranges, the low boiling point impurities may have a boiling point ranging from 200° C. to 255° C., e.g., from 205° C. to 250° C., from 210° C. to 245° C., from 215° C. to 240° C., from 220° C. to 235° C., or from 225° C. to 230° C. In terms of upper limits, the low boiling point impurities may have a boiling point of less than 250° C., e.g., less than 245° C., less than 240° C., less than 235° C., less than 230° C., or less than 225° C. In terms of upper limits, the low boiling point impurities may have a boiling point of greater than 200° C., e.g., greater than 205° C., greater than 210° C., greater than 215° C., or greater than 220° C. In some cases, the low boiling point impurities include cyclohexanone, cyclohexenone, n-hexanenitrile, or 5-hexenenitrile, or combinations thereof.

Intermediate boiling point impurities are those with a boiling point between those of ACN and caprolactam, e.g., between 255° C. and 270° C. In terms of upper limits, the intermediate boiling point impurities may have a boiling point of less than 270° C., e.g., less than 269° C., less than 268° C., less than 267° C., less than 266° C., less than 265° C., less than 264° C., less than 263° C., less than 262° C., or less than 261° C. In terms of lower limits, the intermediate boiling point impurities may have a boiling point of greater than 255° C., e.g., greater than 256° C., greater than 257° C., greater than 258° C., greater than 259° C., or greater than 260° C. Examples of intermediate boiling point impurities include 6-aminocaproic acid.

High boiling point impurities are those with a boiling point higher than that of caprolactam, e.g., greater than 270° C. The high boiling point impurities may, for example, have a boiling point ranging from 270° C. to 500° C., e.g., 275° C. to 475° C., 300° C. to 450° C., 325° C. to 425° C., or 350° C. to 400° C. In terms of upper limits, the high boiling point impurities may have a boiling point of less than 500° C., e.g., less than 475° C., less than 450° C., less than 425° C., or less than 400° C. In terms of lower limits, the high boiling point impurities may have a boiling point of greater than 270° C., e.g., greater than 275° C., greater than 300° C., greater than 325° C., or greater than 350° C. In some cases, the high boiling point impurities include caprolactam dimers, caprolactam oligomers, or N-phenylacetamide, or combinations thereof.

For example, the amount of low boiling impurities in the caprolactam feed stream can range from 0 to 10 wt. %, e.g., 1 wt. % to 9 wt. %, 2 wt. % to 8 wt. %, 3 wt. % to 7 wt. %, or 4 wt. % to 6 wt. %. In terms of upper limits, the amount of low boiling impurities in the caprolactam feed stream can be less than 10 wt. %, less than 9 wt. %, less than 8 wt. %, less than 7 wt. %, or less than 6 wt. %. In terms of lower limits, the amount of low boiling impurities in the caprolactam feed stream can be greater than 1 wt. %, greater than 2 wt. %, greater than 3 wt. %, greater than 4 wt. %, or greater than 5 wt. %. Lower amounts, e.g., less than 1 wt. %, and higher amounts, e.g., greater than 10 wt. %, are also contemplated.

The amount of intermediate boiling impurities in the caprolactam feed stream can, for example, range from 0 to 10 wt. %, e.g., 1 wt. % to 9 wt. %, 2 wt. % to 8 wt. %, 3 wt. % to 7 wt. %, or 4 wt. % to 6 wt. %. In terms of upper limits, the amount of intermediate boiling impurities in the caprolactam feed stream can be less than 10 wt. %, less than 9 wt. %, less than 8 wt. %, less than 7 wt. %, or less than 6 wt. %. In terms of lower limits, the amount of intermediate boiling impurities in the caprolactam feed stream can be greater than 1 wt. %, greater than 2 wt. %, greater than 3 wt. %, greater than 4 wt. %, or greater than 5 wt. %. Lower amounts, e.g., less than 1 wt. %, and higher amounts, e.g., greater than 10 wt. %, are also contemplated.

The amount of high boiling impurities in the caprolactam feed stream can, for example, range from 0 to 20 wt. %, e.g., 1 wt. % to 19 wt. %, 2 wt. % to 18 wt. %, 4 wt. % to 16 wt. %, or 6 wt. % to 14 wt. %, or 8 wt. % to 12 wt. %. In terms of upper limits, the amount of intermediate boiling impurities in the caprolactam feed stream can be less than 20 wt. %, less than 18 wt. %, less than 16 wt. %, less than 14 wt. %, or less than 12 wt. %. In terms of lower limits, the amount of intermediate boiling impurities in the caprolactam feed stream can be greater than 1 wt. %, greater than 2 wt. %, greater than 4 wt. %, greater than 6 wt. %, greater than 8 wt. %, or greater than 10 wt. %. Lower amounts, e.g., less than 1 wt. %, and higher amounts, e.g., greater than 20 wt. %, are also contemplated.

Reaction Conditions

The manner in which the reaction may be conducted may vary widely. In some cases, the reaction may be conducted in a fixed bed reactor. It has been discovered that fixed bed reactors surprisingly provide for improved uniformity of temperature and good contact between the catalyst and reactants. Advantageously, these reactors also contribute low equipment costs for construction, operation, and maintenance.

The reaction may be conducted at a temperature ranging from 250° C. to 500° C., e.g., from 275° C. to 475° C., from 300° C. to 450° C., from 325° C. to 425° C., or from 350° C. to 400° C. In terms of upper limits, reaction may be conducted at a temperature less than 500° C., less than 475° C., less than 450° C., less than 425° C., or less than 400° C. In terms of lower limits, reaction may be conducted at a temperature greater than 250° C., greater than 275° C., greater than 300° C., greater than 350° C., or greater than 375° C. At temperatures below about 300° C., the reaction may not proceed. At temperatures greater than 450° C., the selectivity may decline.

The reaction may be conducted at a pressure ranging from 0 psig to 500 psig, e.g., 1 psig to 450 psig, 5 psig to 400 psig, 10 psig to 350 psig, 50 psig to 300 psig, 100 psig to 250 psig, or 150 psig to 200 psig. In terms of upper limits, the reaction pressure can be less than 500 psig, less than 450 psig, less than 400 psig, less than 350 psig, less than 300 psig, less than 250 psig, or less than 200 psig. In terms of lower limits, the reaction pressure can be greater than 1 psig, greater than 5 psig, greater than 10 psig, greater than 50 psig, greater than 100 psig, or greater than 150 psig. Lower pressures, e.g., less than 1 psig, and higher pressures, e.g. greater than 500 psig, are also contemplated.

As a result of the disclosed process and catalyst, the conversion of caprolactam to the 6-ACN product using the disclosed process may be greater than 50%, e.g., greater than 55%, greater than 60%, greater than 62%, greater than 65%, greater than 70%, greater than 75%, greater than 80%, greater than 85%, greater than 90%, greater than 95%, or greater than 99%. In terms of upper limits, the conversion of caprolactam to the 6-ACN product may be less than 100%, e.g., less than 99%, less than 95%, less than 90%, less than 85%, less than 80%, or less than 75%. In terms of lower limits, the conversion of caprolactam to the 6-ACN product may be greater than 50%, e.g., greater than 55%, greater than 60%, greater than 62%, greater than 65%, or greater than 70%.

The selectivity for the 6-ACN product in the disclosed process may be greater than 90%, e.g., greater than 91%, greater than 92%, greater than 93%, greater than 94%, greater than 95%, greater than 96%, greater than 97%, greater than 98%, greater than 99%, greater than 99.5%, or greater than 99.9%. In terms of upper limits, the selectivity for the 6-ACN product may be less than 100%, e.g., less than 99.9%, less than 99.5%, less than 99%, less than 98%, less than 97%, or less than 96%. In terms of lower limits, the selectivity for the 6-ACN product may be greater than 90%, e.g., greater than 91%, greater than 92%, greater than 93%, greater than 94%, or greater than 95%.

The resulting 6-ACN product may be surprisingly pure, especially in view of the lower purity caprolactam feed. In some cases, the 6-ACN product may comprise impurities such as cyclohexanone, cyclohexenone, n-hexanenitrile, 5-hexenenitrile, 6-aminocaproic acid, caprolactam dimers, caprolactam oligomers, or N-phenylacetamide, or combinations thereof, in an amount less than 10 wt. %, e.g., less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.1 wt. %, less than 500 ppm, less than 250 ppm, less than 100 ppm, less than 50 ppm, less than 10 ppm or less than 1 ppm. In terms of upper limits, the 6-ACN product may comprise impurities in an amount less than 10 wt. %, e.g., less than 9 wt. %, less than 8 wt. %, less than 7 wt. %, less than 6 wt. %, less than 5 wt. %, less than 4 wt. %, less than 3 wt. %, or less than 2 wt. %. In terms of lower limits, the 6-ACN product may comprise impurities in an amount greater than 1 ppm, e.g., greater than 10 ppm, greater than 100 ppm, greater than 250 ppm, greater than 500 ppm, greater than 0.1 wt. %, or greater than 1 wt. %. These ranges and limits are applicable to individual impurities or to combinations thereof or to impurities as a whole.

If desired, the 6-ACN product may be further purified, e.g., by distillation. The purified 6-ACN product may comprise impurities in an amount less than 10 wt. %, e.g., less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.1 wt. %, less than 500 ppm, less than 250 ppm, less than 100 ppm, less than 50 ppm, less than 10 ppm or less than 1 ppm. In terms of upper limits, the purified 6-ACN product may comprise impurities in an amount less than 10 wt. %, e.g., less than 9 wt. %, less than 8 wt. %, less than 7 wt. %, less than 6 wt. %, less than 5 wt. %, less than 4 wt. %, less than 3 wt. %, or less than 2 wt. %. In terms of lower limits, the purified 6-ACN product may comprise impurities in an amount greater than 1 ppm, e.g., greater than 10 ppm, greater than 100 ppm, greater than 250 ppm, greater than 500 ppm, greater than 0.1 wt. %, or greater than 1 wt. %.

Conversion of ACN to HMD

In some cases, the produced ACN may be further reacted, e.g., to form HMD. And, in some cases the produced ACN may be purified prior to the ACN-to-HMD conversion. For example, the ACN may be purified by distillation. Purification of ACN prior to the production of HMD may allow for the production of higher purity HMD, which beneficially simplifies the purification of the HMD.

In some cases, the ACN produced by the process described herein may be further reacted to form HMD. This reaction and the parameters associated therewith are known. For example, U.S. Pat. No. 6,281,388 discloses processes for the hydrogenation of nitriles to amines, which may be used for the conversion of ACN to HMD.

For example, the ACN may be contacted with hydrogen in the presence of a catalyst to provide hexamethylenediamine. In some cases, the reaction may be conducted in a liquid reaction medium, such as water, to produce the HMD.

The catalyst may be a finely divided metal catalyst. Specifically, the catalyst may comprise a cobalt catalyst or a nickel catalyst, such as Raney nickel. The catalyst may further comprise promotor metals, such as chromium, iron, or a combination thereof. The amount of catalyst per 100 parts by weight of the reaction mixture can, for example, range from 1 to 100 parts by weight. Preferably, the amount of catalyst per 100 parts by weight of the reaction mixture can range from 3 to 35 parts by weight, e.g., 4 parts to 35 parts, 5 parts to 30 parts, 10 parts to 25 parts, or 15 parts to 20 parts. In terms of upper limits, the amount of catalyst per 100 parts by weight of the reaction mixture can be less than 100 parts, e.g., less than 80 parts, less than 60 parts, less than 50 parts, or less than 35 parts. In terms of lower limits, the amount of catalyst may be greater than 1 part, e.g., greater than 3 parts, greater than 5 parts, greater than 10 parts, greater than 15 parts, greater than 20 parts, greater than 25 parts, or greater than 35 parts.

The liquid reaction medium may include an inorganic base. Suitable inorganic bases include alkali metal hydroxides, such as sodium, potassium, lithium, rubidium, or cesium hydroxides. The inorganic base may comprise a mixture of two or more alkali metal hydroxides, such as a mixture of sodium hydroxide and potassium hydroxide.

The amount of inorganic base per kilogram of catalyst can range from 0.2 to 12 moles per kilogram of catalyst, e.g., 0.5 moles to 10 moles, 1 mole to 7 moles, 2 moles to 5 moles, or 2.5 moles to 3.5 moles. In terms of upper limits, the amount of inorganic base per kilogram of catalyst can be less than 12 moles, e.g., less than 10 moles, less than 7 moles, less than 5 moles, or less than 3.5 moles. In terms of lower limits, amount of inorganic base per kilogram of catalyst can be greater than 0.2 moles, e.g., greater than 0.5 moles, greater than 1 mole, greater than 2 moles, or greater than 2.5 moles. Lower amounts, e.g., less than 0.2 moles, and higher amounts, e.g., greater than 12 moles, are also contemplated.

The liquid reaction medium may comprise water. The amount of water per mole of inorganic base can, for example, range from 2 to 130 moles, e.g., 5 moles to 120 moles, 10 moles to 100 moles, 20 moles to 80 moles, 30 moles to 70 moles, or 40 moles to 60 moles. In terms of upper limits, the amount of water per mole of inorganic base can be less than 130 moles, e.g., less than 120 moles, less than 100 moles, less than 80 moles, less than 70 moles, or less than 60 moles. In terms of lower limits, the amount of water per mole of inorganic base can be greater than 2 moles, e.g., greater than 5 moles, greater than 10 moles, greater than 20 moles, greater than 30 moles, or greater than 40 moles.

The liquid reaction medium may comprise an aqueous solution of the inorganic base. The concentration of the base can, for example, be from 25% to 70% by weight of the aqueous solution, e.g. from 30% to 65%, from 35% to 60%, from 40% to 55%, or from 45% to 50%. In terms of upper limits, the amount of water per mole of inorganic base can be less than 70%, e.g., less than 65%, less than 60%, less than 55%, or less than 50%. In terms of lower limits, the amount of water per mole of inorganic base can be greater than 25%, e.g., greater than 30%, greater than 35%, greater than 40%, or greater than 45%.

The reaction pressure can, for example, range from 275 psig to 750 psig, e.g., 300 psig to 700 psig, 350 psig to 650 psig, 400 psig to 600 psig, or 450 psig to 550 psig. In terms of upper limits, the reaction pressure can be less than 750 psig, e.g., less than 700 psig, less than 650 psig, less than 600 psig, or less than 550 psig. In terms of lower limits, the reaction pressure can be greater than 275 psig, e.g., greater than 300 psig, greater than 350 psig, greater than 400 psig, or greater than 450 psig. Lower pressures, e.g., less than 275 psig, and higher pressures, e.g., greater than 750 psig, are also contemplated.

The reaction temperature can, for example, range from 60° C. to 120° C., e.g., 70° C. to 110° C., or 80° C. to 100° C. In terms of upper limits, the reaction temperature can be less than 120° C., e.g., less than 110° C., or less than 100° C. In terms of lower limits, the reaction temperature can be greater than 60° C., e.g., greater than 70° C., or greater than 80° C. Lower temperatures, e.g., less than 60° C., and higher temperatures, e.g., greater than 120° C., are also contemplated.

The HMD thus produced may comprise less than 10 wt. % impurities, e.g., less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.1 wt. %, less than 500 ppm, less than 250 ppm, less than 100 ppm, less than 50 ppm, less than 10 ppm or less than 1 ppm. In terms of upper limits, the HMD may comprise impurities in an amount less than 10 wt. %, e.g., less than 9 wt. %, less than 8 wt. %, less than 7 wt. %, less than 6 wt. %, less than 5 wt. %, less than 4 wt. %, less than 3 wt. %, or less than 2 wt. %. In terms of lower limits, the HMD may comprise impurities in an amount greater than 1 ppm, e.g., greater than 10 ppm, greater than 100 ppm, greater than 250 ppm, greater than 500 ppm, greater than 0.1 wt. %, or greater than 1 wt. %.

In some cases, the process disclosed herein may be employed in an integrated process, in which the product ACN (or HMD) is employed as a starting material for a subsequent reaction. These starting materials may then be reacted under various reaction conditions to provide entirely different reaction products. For example, the HMD thus produced may be further reacted to form polymers such as non-PA6 polyamides, e.g., PA6,6; PA6,10; PA6,12; and co- and terpolymers thereof. In some cases, the produced HMD may be used in the production of hexamethylene diisocyanate, which in turn is used in the manufacture of polyurethanes.

As used herein, “greater than” and “less than” limits may also include the number associated therewith. Stated another way, “greater than” and “less than” may be interpreted as “greater than or equal to” and “less than or equal to.” It is contemplated that this language may be subsequently modified in the claims to include "or equal to." For example, "greater than 4.0" may be interpreted as, and subsequently modified in the claims as "greater than or equal to 4.0."

Some of the components and steps disclosed herein may be considered optional. In some cases, the disclosed compositions, processes, etc. may expressly exclude one or more of the aforementioned components or steps in this description, e.g., via claim language. This is contemplated herein by the inventors. For example, claim language may be modified to recite that the disclosed compositions, processes, streams, etc., do not utilize or comprise one or more of the aforementioned components or steps, e.g., e.g., the caprolactam feed stream does not include 1,2,3,4,6,7,8,9-octahydrophenazine (or any other of the aforementioned additives). Such negative limitations are contemplated, and this text serves as support for negative limitations for components, steps, and/or features.

EXAMPLES

Conversion of Caprolactam to ACN

Experimental runs were carried out using, as catalysts, working Examples 1-5 and Comparative Examples A-C. Examples 1-5 were aluminosilicate zeolite catalysts (ZSM-5 or mordenite) comprising little or no active metals and/or little or no phosphorous. The catalysts of Examples 1, 2, and 4 were CBV 2314 CY1.6 produced by Zeolyst International. Example 3 was HSZ-822HOD1A produced by Tosoh. Example 5 was CBV21 CY1.6 produced by Zeolyst International. The catalysts in Examples 1-5 comprised less than 1 ppm phosphorous and less than 1 ppm active metals.

The catalysts of Comparative Examples A-C were conventionally used non-aluminosilicate catalysts alumina ($Al_2O_3$), silicon dioxide ($SiO_2$) and boron phosphate. Comparative Example A was a high surface area γ-phase alumina catalyst support produced by Alfa Aesar. Comparative Example B was a high surface area silica, grade 40, mesh 6-12 produced by Grace. Comparative Example C was boron phosphate produced by BassTech International. Comparative Example D was an aluminum phosphate catalyst produced by Sigma Aldrich and converted to extrudates using 4% microcrystalline cellulose and 10% alumina, followed by calcination for four hours at 450° C. Comparative Example E was a modified ZSM-5 (mZSM5) catalyst. Specifically, the catalyst was modified with calcium and magnesium phosphate, and was prepared by stirring 100 g of ZSM-5 catalyst for 1 hour in 1 liter of a solution containing calcium acetate (0.05 M), magnesium acetate (0.05 M), and ammonium dihydrogen phosphate (0.05 M), after which the modified catalyst was filtered off, rinsed with water, and dried at 110° C., and calcined at 500° C. for 20 hour prior to being used in the reaction.

In each case, the catalyst was charged into a fixed bed reactor, and a flow of ammonia and caprolactam feed (~99.5% purity) was passed over the catalyst under atmospheric pressure. Additional reaction conditions are shown in Table 1. The reaction yielded a 6-aminocapronitrile product stream. The product stream was compositionally analyzed, e.g., for 6-aminocapronitrile content, as well as for impurity content.

Following the reaction, the conversion of caprolactam and selectivity for 6-aminocapronitrile were calculated as shown below in Equations 1 and 2 following gas chromatography (GC) analysis to determine the amounts of the components. The calculated conversions and selectivities are also provided in Table 1. The 6-ACN product was found to have surprisingly high purity, especially in view of the feed material. Based on the GC analysis, the impurities were believed to comprise 6-aminocaproic acid, (cyclic) caprolactam dimers, caprolactam oligomers, and N-methylcaprolactam, or combinations thereof.

TABLE 1

| Example # | Catalyst | Ammonia flow rate, cc/min | Capro flow rate, g/min | Temp., ° C. | Conv., % | Select., % |
|---|---|---|---|---|---|---|
| Ex. 1 | ZSM5 (20 g) | 620 | 0.26 | 375 | 68 | 95.7 |
| Ex. 2 | ZSM5 (20 g) | 2728 | 1.14 | 375 | 57.7 | 96.7 |
| Ex. 3 | ZSM5 (20 g) | 620 | 0.26 | 350 | 55.8 | 96.6 |
| Ex. 4 | ZSM5 (59.15 g) | 1430 | 0.6 | 375 | 58.2 | 94.9 |
| Ex. 5 | Mord. (60.03 g) | 1430 | 0.6 | 375 | 60.9 | 95.0 |
| Comp. Ex. A | $Al_2O_3$ (20 g) | 620 | 0.26 | 375 | 61.3 | 90.8 |
| Comp. Ex. B | $SiO_2$ (20 g) | 620 | 0.26 | 375 | 41.3 | 89.9 |
| Comp. Ex. C | B Phos (51.65) | 1550 | 0.65 | 350 | 15.1 | 95.9 |
| Comp. Ex. D | $AlPO_4$ (52.35) | 1550 | 0.65 | 350 | 19.7 | 98.6 |
| Comp. Ex. E | mZSM5 (52.63) | 1550 | 0.65 | 350 | 34.2 | 96.4 |

As shown in Table 1, the aluminosilicate zeolite catalysts of Examples 1-5 demonstrate synergistic combination of significantly higher selectivity and conversion than the non-aluminosilicate zeolite catalysts of the Comparative Examples. Comp. Ex. A demonstrates a suitable conversion, but its selectivity is significantly worse than Exs. 1-5 (90.8 versus 94.9-96.7). Comp. Ex. B demonstrates much poorer performance—both significantly lower selectivity and conversion in comparison to Examples 1-5. Comp. Ex. C and D each demonstrate far lower conversion than the aluminosilicate zeolite catalysts. Finally, Comp. Ex. E, a modified aluminosilicate zeolite catalysts, shows far lower conversion than the unmodified aluminosilicate zeolite catalysts. This is surprising and unexpected because catalyst modifiers would be expected to provide conversion improvements, not reductions.

Furthermore, as shown by the selectivity for ACN (94.9% to 96.7% in Ex. 1-5), the amount of impurities in the final product was low, e.g., less than 6%.

Hydrogenation of Adiponitrile and 6-aminocapronitrile

Two experimental runs were completed to demonstrate the efficacy of hydrogenation conditions for the formation of HMD from adiponitrile, 6-aminocapronitrile (see above), or mixtures thereof.

In each case, a sponge nickel catalyst (112.5) g was slurried in 1 L of HMD in a reactor. The reactor was pressurized under hydrogen atmosphere to 500 psig, and heated to 90° C. The reactants were fed to the reactor at a rate of 15 mL/min, and hydrogen was supplied to the reactor to maintain a constant pressure of 500 psig. Following the reaction, the percent conversion of the reactants was determined, as well as the purity of the HMD produced as measured by GC.

The reactants and results for each run are shown below in Table 2. Each set of reactants included 3.5% water.

TABLE 2

| Example # | Reactants | Conv., % | Purity. % |
|---|---|---|---|
| Ex. 6 | ADN 61% + ACN 39% | 100 | >99.5 |
| Ex. 7 | ACN | 100 | >99.5 |

As shown in Table 2, the 6-ACN product made from the disclosed process can be suitably converted to HMD, if desired.

EMBODIMENTS

As used below, any reference to a series of embodiments is to be understood as a reference to each of those embodiments disjunctively (e.g., "Embodiments 1— 4" is to be understood as "Embodiments 1, 2, 3, or 4").

Embodiment 1: a gas-phase process for converting caprolactam to 6-aminocapronitrile (6-ACN), the process comprising: contacting a caprolactam feed with ammonia and an aluminosilicate zeolite catalyst to produce an aminocapronitrile product, e.g., a 6-aminocapronitrile product, wherein the catalyst comprises less than 5 wt. % of an active metal.

Embodiment 2: the process of Embodiment 1, wherein the aluminosilicate zeolite catalyst comprises less than 1 wt. % phosphorous.

Embodiment 3: the process of Embodiment 1 or Embodiment 2, wherein the aluminosilicate zeolite catalyst has a silica to alumina ratio (SAR) less than 200.

Embodiment 4: the process of Embodiments 1-3, wherein the reaction is conducted at a temperature ranging from 350° C. to 375° C.

Embodiment 5: the process of Embodiments 1-4, wherein the caprolactam feed comprises from 100 ppm to 40 wt. % impurities comprising 6-aminocaproic acid, caprolactam dimers, caprolactam oligomers, N-methylcaprolactam, N-ethylcaprolactam, hexenoic acid, cyclohexylamine, or combinations thereof.

Embodiment 6: the process of Embodiments 1-5, wherein the 6-aminocapronitrile product comprises less than 10 wt. % impurities.

Embodiment 7: a gas-phase process for converting caprolactam to a 6-aminocapronitrile (6-ACN) product, the process comprising: contacting a caprolactam feed comprising less than 100 wt % caprolactam and from 100 ppm to 40 wt. % impurities comprising 6-aminocaproic acid, caprolactam dimers, N-methylcaprolactam, N-ethylcaprolactam, or combinations thereof, with ammonia and a catalyst to produce a 6-aminocapronitrile product.

Embodiment 8: the process of Embodiment 7, wherein the impurities comprise less than 10 wt. % of low boiling impurities having a boiling point less than 255° C., measured at atmospheric pressure.

Embodiment 9: the process of Embodiment 7 or Embodiment 8, wherein the impurities comprise less than 10 wt % intermediate boiling point impurities having a boiling point ranging from 255° C. to 270° C., measured at atmospheric pressure Embodiment 10: the process of Embodiments 7-9, wherein the impurities comprise less than 20 wt. % of high boiling point impurities having a boiling point greater than 270° C., measured at atmospheric pressure.

Embodiment 11: the process of Embodiments 7-10, wherein the caprolactam comprises recycled PA6, or 6-aminocaproic acid, or a mixture thereof.

Embodiment 12: the process of Embodiments 7-11, wherein the 6-aminocapronitrile product comprises less than 10 wt. % impurities.

Embodiment 13: the process of Embodiments 7-12 further comprising purifying the 6-aminocapronitrile product via distillation.

Embodiment 14: an integrated process for converting polyamide-6 (PA6) to hexamethylenediamine, the process comprising: depolymerizing a stream comprising PA6 and impurities to produce a depolymerized stream comprising caprolactam monomers, dimers, oligomers, or combinations thereof; contacting the depolymerized stream with ammonia and an aluminosilicate zeolite catalyst comprising less than 5 wt. % of an active metal to produce a 6-aminocapronitrile product; optionally reacting the 6-aminocapronitrile product to produce hexamethylenediamine; and reacting the 6-aminocapronitrile product and/or the hexamethylenediamine to form a subsequent reaction product.

Embodiment 15: the process of Embodiment 14, wherein the impurities comprise 6-aminocaproic acid, caprolactam dimers, caprolactam oligomers, N-methylcaprolactam, N-ethylcaprolactam, hexenoic acid, cyclohexylamine, or combinations thereof.

Embodiment 16: the process of Embodiment 14 or Embodiment 15, wherein the 6-aminocapronitrile product comprises less than 10 wt. % impurities.

Embodiment 17: the process of Embodiments 14-16, further comprising purifying the 6-aminocapronitrile product, preferably by distillation.

Embodiment 18: the process of Embodiments 14-17, wherein the reacting comprises hydrogenating the 6-aminocapronitrile product in the presence of a nickel-based catalyst to produce the hexamethylenediamine.

Embodiment 19: the process of Embodiments 14-18, wherein the 6-aminocapronitrile product further comprises adiponitrile (ADN).

Embodiment 20: the process of claim 14, wherein the reacting of the 6-aminocapronitrile product and/or the hexamethylenediamine comprises reacting the hexamethylenediamine to form non-PA6 polyamides, e.g., PA6,6; PA6,10; PA6,12; and co- and terpolymers thereof, hexamethylene diisocyanate, or polyurethanes.

We claim:

1. A process for converting caprolactam to 6-aminocapronitrile, the process comprising:
- contacting a caprolactam feed with ammonia and an aluminosilicate zeolite catalyst to produce a 6-aminocapronitrile product,
- wherein the caprolactam feed comprises caprolactam, caprolactam dimers, and caprolactam oligomers;
- wherein the aluminosilicate zeolite catalyst contains no active metal or phosphorus; and
- wherein conversion is greater than 50% and selectivity for 6-aminocapronitrile is greater than 91%.

2. The process of claim 1, wherein the caprolactam feed comprises from 100 ppm to 40 wt. % impurities, and wherein the impurities of the caprolactam feed comprise the caprolactam dimers and the caprolactam oligomers, and further comprise 6-aminocaproic acid, N-methylcaprolactam, N-ethylcaprolactam, hexenoic acid, or cyclohexylamine, or combinations thereof.

3. The process of claim 1, wherein the aluminosilicate zeolite catalyst has a silica to alumina ratio (SAR) less than 200.

4. The process of claim 1, wherein the reaction is conducted at a temperature ranging from 350° C. to 375° C.

5. The process of claim 2, wherein the caprolactam feed comprises from 500 ppm to 10 wt. % of the impurities.

6. The process of claim 1, wherein the 6-aminocapronitrile product comprises greater than 0.1 wt. % and less than 10 wt. % impurities comprising 6-aminocaproic acid, caprolactam dimers, caprolactam oligomers, and N-methylcaprolactam.

7. A gas-phase process for converting caprolactam to a 6-aminocapronitrile product, the process comprising:

contacting a caprolactam feed with ammonia and an aluminosilicate zeolite catalyst to produce a 6-aminocapronitrile product, the caprolactam feed comprising less than 100 wt % caprolactam and from 100 ppm to 40 wt. % impurities comprising low boiling impurities having a boiling point less than 255° C., intermediate boiling point impurities having a boiling point ranging from 255° C. to 270° C., and high boiling point impurities having a boiling point greater than 270° C., the boiling points measured at atmospheric pressure, wherein the aluminosilicate zeolite catalyst contains no active metal or phosphorus, and wherein conversion is greater than 50% and selectivity for 6-aminocapronitrile is greater than 91%.

8. The process of claim 7, wherein the impurities of the caprolactam feed comprise less than 10 wt. % of the low boiling impurities having a boiling point less than 255° C.

9. The process of claim 7, wherein the impurities of the caprolactam feed comprise less than 10 wt % of the intermediate boiling point impurities.

10. The process of claim 7, wherein the impurities of the caprolactam feed comprise less than 20 wt. % of the high boiling point impurities.

11. The process of claim 7, wherein the caprolactam feed comprises recycled PA6.

12. The process of claim 7, wherein the 6-aminocapronitrile product comprises greater than 0.1 wt. % and less than 10 wt. % impurities comprising 6-aminocaproic acid, caprolactam dimers, caprolactam oligomers, and N-methylcaprolactam.

13. The process of claim 7, further comprising purifying the 6-aminocapronitrile product via distillation to separate 6-aminocapronitrile from 6-aminocaproic acid, caprolactam dimers, caprolactam oligomers, and N-methylcaprolactam.

14. An integrated process for converting polyamide-6 (PA6) to hexamethylenediamine, the process comprising:

depolymerizing a stream comprising PA6 and impurities to produce a depolymerized stream comprising caprolactam monomers, dimers, and oligomers;

contacting the depolymerized stream with ammonia and an aluminosilicate zeolite catalyst containing no active metal or phosphorus comprising less than 5 wt. % of an active metal to produce a 6-aminocapronitrile product;

reacting the 6-aminocapronitrile product to produce hexamethylenediamine; and reacting the hexamethylenediamine to form non-PA6 polyamides, polyurethanes, or hexamethylene diisocyanate.

15. The process of claim 14, wherein the depolymerized stream further comprises N-methylcaprolactam, N-ethylcaprolactam, hexenoic acid, cyclohexylamine, or combinations thereof.

16. The process of claim 14, wherein the 6-aminocapronitrile product comprises at least 5000 ppm and less than 10 wt. % impurities comprising 6-aminocaproic acid, caprolactam dimers, caprolactam oligomers, and N-methylcaprolactam.

17. The process of claim 14, further comprising purifying the 6-aminocapronitrile product by distillation to separate 6-aminocapronitrile from 6-aminocaproic acid, caprolactam dimers, caprolactam oligomers, and N-methylcaprolactam.

18. The process of claim 14, wherein the reacting comprises hydrogenating the 6-aminocapronitrile product in the presence of a nickel-based catalyst to produce the hexamethylenediamine.

19. The process of claim 14, wherein the reacting of the 6-aminocapronitrile product to produce the hexamethylenediamine comprises reacting a mixture of the 6-aminocapronitrile product and adiponitrile (ADN) to produce the hexamethylenediamine.

20. The process of claim 14, wherein the non-PA6 polyamides are selected from PA6,6; PA6,10; PA6, 12; and co- and terpolymers thereof.

* * * * *